US007155982B2

(12) United States Patent
Oesmann et al.

(10) Patent No.: US 7,155,982 B2
(45) Date of Patent: Jan. 2, 2007

(54) TESTING APPARATUS FOR COMPRESSION AND SHEAR TESTING OF A TEST COMPONENT SUCH AS A CURVED AIRCRAFT COMPONENT

(75) Inventors: Werner Oesmann, Hamburg (DE); Jean-Charles Schleret, Hamburg (DE); Andreas Kotzke, Elmshorn (DE); Peter Peters, Horneburg (DE)

(73) Assignee: Airbus Deutschland GmbH, Hamburg (DE)

( * ) Notice: Subject to any disclaimer, the term of this patent is extended or adjusted under 35 U.S.C. 154(b) by 0 days.

(21) Appl. No.: 10/951,920

(22) Filed: Sep. 27, 2004

(65) Prior Publication Data

US 2005/0109118 A1    May 26, 2005

(30) Foreign Application Priority Data

Sep. 26, 2003  (DE) ................ 103 44 855

(51) Int. Cl.
*G01N 3/24* (2006.01)
*G01N 3/08* (2006.01)

(52) U.S. Cl. .......................... 73/841; 73/818
(58) Field of Classification Search ............... 73/841, 73/815, 818
See application file for complete search history.

(56) References Cited

U.S. PATENT DOCUMENTS 3,048,033 A    8/1962  Melzer
4,478,086 A * 10/1984  Gram ........................... 73/781
4,864,866 A *  9/1989  Hardy et al. .................. 73/831
5,677,494 A * 10/1997  Keener et al. ................. 73/810
5,712,431 A *  1/1998  Vilendrer ...................... 73/841
6,467,357 B1* 10/2002  Pe ................................ 73/859
2002/0170361 A1* 11/2002  Vilendrer et al. ............. 73/849

FOREIGN PATENT DOCUMENTS

| CH | 374221 | 12/1963 |
|----|--------|---------|
| DE | 197 27 754 | 1/1999 |

* cited by examiner

*Primary Examiner*—Max Noori
(74) *Attorney, Agent, or Firm*—W. F. Fasse; W. G. Fasse

(57) ABSTRACT

A testing apparatus receives a test component between a force introduction table and a pressure plate, which apply a compressive load to the component therebetween. First and second shear beams are secured to opposite vertical edges of the component to respectively introduce upwardly and downwardly directed shear forces into the component. The upwardly directed shear force is generated by a first hydraulic cylinder that is arranged above the pressure plate in a horizontally adjustable manner on a head frame, and that is connected to the first shear beam through two tension rod assemblies including tensile force measuring transducers. The downwardly directed shear force is generated by two second hydraulic cylinders that are arranged under the pressure plate and that are connected to the second shear beam by strut assemblies including compressive force measuring transducers. High shear loads can be applied in the same vertical plane as the compressive load.

19 Claims, 1 Drawing Sheet

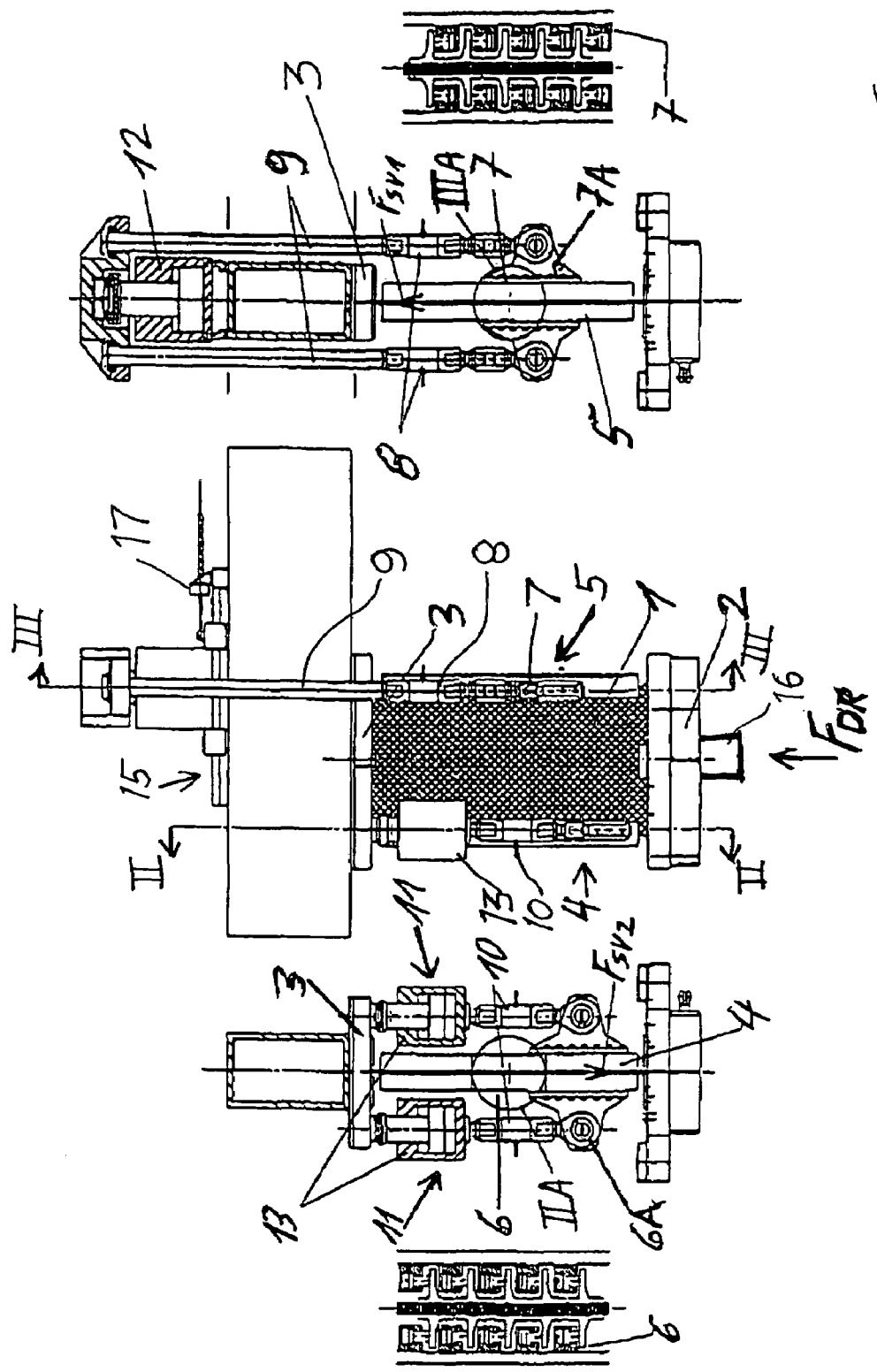

TESTING APPARATUS FOR COMPRESSION AND SHEAR TESTING OF A TEST COMPONENT SUCH AS A CURVED AIRCRAFT COMPONENT

PRIORITY CLAIM

This application is based on and claims the priority under 35 U.S.C. §119 of German Patent Application 103 44 855.0, filed on Sep. 26, 2003, the entire disclosure of which is incorporated herein by reference.

FIELD OF THE INVENTION

The present invention relates to an apparatus for introducing compression and shear forces into a test component or test specimen such as a curved aircraft component, for carrying out the compression and shear load testing of the component.

BACKGROUND INFORMATION

Various load testing apparatuses are known, including apparatuses for carrying out simultaneous compressive loading and shear loading of a test component that is to be load tested.

Generally, in such known apparatuses, the compression load may be introduced into the test component by means of a force introduction table and a pressure plate acting as a counter-support, between which the test component is received. For example, a force-regulated hydraulic cylinder acts on the force introduction table to move it toward the pressure plate, for example in a vertical direction, to thereby apply a regulated vertical compression load to the test component that is received between the force introduction table and the pressure plate. Furthermore, vertically oriented shear loads can be applied to the lateral vertical edges of the test component via two shear beams that are respectively secured to the two opposite vertical edges of the test component. One of these shear beams applies an upwardly directed force, while the other one of these shear beams applies a downwardly directed force, so as to apply the intended shear to the test component between its two opposite vertical edges.

More particularly, such a combined compression and shear load testing of a test component such as a curved aircraft component can be carried out using a particular conventionally known compression and shear testing apparatus, as follows. The main compression load is introduced vertically into the aircraft component through a force introduction table, which is moved by a force-regulated hydraulic cylinder, preferably in a vertical direction, toward a pressure plate that acts as a counter-support, with the aircraft component received between the force introduction table and the pressure plate. To introduce the compressive force into the aircraft component, the component is provided with special rim or edge reinforcements, so that the compressive force between the force introduction table and the pressure plate can be introduced into the body of the component without damaging its upper and lower edges.

Furthermore, the pressure plate is secured, e.g. bolted, to a head frame, which may be a stationary component of the machine frame. On the other hand, the compression loading hydraulic cylinder is supported on a base that is supported on a transverse girder which is supported from the machine frame by pivotally connected tension rods with integrated tensile force measuring transducers such as load cells.

Additionally, a horizontal shear component can be introduced into the aircraft component by two hydraulic cylinders that are pivotally or articulately connected to the force introduction table.

Vertical shear forces including an upwardly directed shear component and a downwardly directed shear component are introduced into the opposite vertical edges of the aircraft component by two shear beams, respectively, having integrated force-regulated hydraulic cylinders. The effective direction of force application of the cylinders and thus of the shear beams is opposite one another, to apply the oppositely directed shear forces as mentioned above. The hydraulic cylinders are integrated into the shear beams, and particularly are installed pair-wise at a spacing or raster of e.g. 100 mm in the shear beams extending along the vertical edges of the aircraft component. For introducing the loads from the shear beams into the aircraft component, T-shaped load introduction brackets or fixtures are secured, e.g. screwed or bolted, to the aircraft component along the vertical edges thereof, similarly at a spacing or raster of 100 mm.

The force of the upwardly directed shear component is counter-supported or braced through two tension rods provided with tensile force measuring transducers or load cells that are pivotally connected to the first shear beam. The tension rods are further connected to the machine frame in a manner that is adjustable in a horizontal plane. On the other hand, the force of the downwardly directed shear component is counter-supported or braced through two compression struts or links that are provided with compressive force measuring transducers or load cells and that are pivotally connected to the second shear beam.

It is a disadvantage of the previously known conventional apparatuses that they can only be used for a hydraulic pressure up to about 350 bar, because a direct regulation is no longer possible for higher pressures in the hydraulic system. The regulation and the self-compensation of the forces is also in need of improvement.

SUMMARY OF THE INVENTION

In view of the above, it is an object of the invention to provide a compression and shear testing apparatus of the above mentioned general type, in which the compression and shear loads act on the test component in the same direction or plane, e.g. parallel to one another, and are applied to the test component by individually or separately regulatable elements. The invention further aims to avoid or overcome the disadvantages of the prior art, and to achieve additional advantages, as apparent from the present specification. The attainment of these objects is, however, not a required limitation of the claimed invention.

The above objects have been achieved according to the invention in a testing apparatus that receives a test component between a force introduction table and a pressure plate, which apply a compressive load to the component therebetween. First and second shear beams are secured to opposite vertical edges of the component to respectively introduce upwardly and downwardly directed shear forces into the component. The upwardly directed shear force is generated by a first hydraulic cylinder that is arranged above the pressure plate in a horizontally adjustable manner on a head frame, and that is connected to the first shear beam through two tension rod assemblies including tensile force measuring transducers. The downwardly directed shear force is generated by two second hydraulic cylinders that are arranged under the pressure plate and that are connected to the second shear beam by strut assemblies including compressive force measuring transducers. High shear loads can be applied in the same vertical plane as the compressive load.

The above objects have further been achieved according to a first aspect of the invention in a shear testing arrangement for shear testing a test component, comprising:
  a support structure having opposite first and second sides;
  first and second fixtures located at the first side of the support structure and adapted to be fixed to opposite first and second edge portions of the test component;
  a first hydraulic cylinder arranged on and supported against the second side of the support structure;
  two tension rod assemblies that are connected to and extend between the first hydraulic cylinder and the first fixture, and that each respectively include a tension rod and a tensile force measuring transducer in series with one another; and
  two compression strut arrangements that are arranged on and supported against the first side of the support structure, and that extend between the support structure and the second fixture, and that are connected to the second fixture, and that each respectively comprise a respective second hydraulic cylinder and a respective compression force measuring transducer in series with one another.

Still further, the above objects have been achieved according to a second aspect of the invention in a testing apparatus for compression and shear testing of a test component that is to be tested, comprising:
  a pressure plate;
  a force introduction table that is movably arranged relative to the pressure plate to allow relative movement thereof in a compression direction, wherein the pressure plate and the force introduction table are adapted to receive the test component therebetween;
  a compression loading hydraulic cylinder that is connected to and acts on at least one of the force introduction table and the pressure plate, and that is adapted to cause the relative movement of the force introduction table relative to the pressure plate in the compression direction so as to apply a compression load to the test component in the compression direction;
  a first shear beam that is adapted to be secured to the test component;
  a second shear beam that is adapted to be secured to the test component spaced apart from the first shear beam;
  a first hydraulic cylinder that is supported relative to the pressure plate and that is arranged on a side of the pressure plate opposite the force introduction table;
  two tension rod assemblies that extend spaced apart from one another on opposite sides of the pressure plate, and that connect the first hydraulic cylinder to the first shear beam, wherein the first hydraulic cylinder is adapted to generate and apply a first shear force through the tension rod assemblies and the first shear beam to the test component in a first shear direction; and
  two compression strut arrangements that are supported relative to the pressure plate and are connected respectively to opposite sides of the second shear beam, wherein the two compression strut arrangements respectively include two second hydraulic cylinders that are adapted to generate and apply a second shear force through the second shear beam to the test component in a second shear direction opposite the first shear direction.

In the preferred embodiment of the invention, the most important features are as follows. The upwardly directed vertical shear force is generated and applied to the test component by a first force-regulated hydraulic cylinder arranged above the pressure plate acting as a counter-support for the vertical compression force introduction. More particularly, this first hydraulic cylinder is supported in a horizontally adjustable and selectively positionable manner on a head frame that cooperates with the pressure plate. Furthermore, two laterally arranged tension rods transmit the force generated by this first hydraulic cylinder to the first shear beam that couples the upwardly directed shear forces into one of the vertical edges of the test component. The tension rods are pivotally connected to the housing or bracket of the first shear beam, or particularly the housing or bracket of another hydraulic cylinder integrated in this first shear beam. The downwardly directed vertical shear force is generated and applied to the test component by two second force-regulated hydraulic cylinders arranged at the side of, and connected to, the second shear beam that introduces the downwardly directed shear component into the opposite vertical edge of the test component. These two second hydraulic cylinders are preferably directly supported or braced against the pressure plate, and are pivotally connected to the housing or bracket of the second shear beam, or particularly the housing or bracket of another hydraulic cylinder integrated in this second shear beam.

According to a further preferred embodiment of the invention, the head frame is arranged and supported concentrically over the load introduction centerpoint of the test component, preferably the aircraft component being tested. A further preferred feature of the invention is that the tension rods are rotatably or pivotally supported via respective tensile force measuring transducers or load cells on the housing or bracket of the hydraulic cylinder integrated in the first shear beam. Still another preferred feature of the invention is that the force-regulated second hydraulic cylinders are rotatably or pivotally connected respectively via compressive force measuring transducers or load cells on the housing or bracket of the hydraulic cylinder integrated in the second shear beam.

A substantial advantage of the inventive arrangement is that the elements for introducing the shear forces act to compensate a length change or variation (especially an uneven length change), arising due to the compression loading, of the aircraft component being tested. In this regard, in an advantageous manner, the shear load is introduced into the vertical edges of the aircraft component according to prescribed requirements at a specified pattern spacing or raster of preferably 100 mm. The general arrangement of the hydraulic cylinders integrated into the respective shear beams may be advantageously maintained, although this is not absolutely necessary in the inventive apparatus. The integrated hydraulic cylinders of the shear beams are modified according to the invention so that the required shear load of, for example, 1700 N/mm can be transmitted through these cylinders. This requires a hydraulic pressure of about 900 bar. In this pressure range, a direct servo-hydraulic proportional regulation is not possible. An advantage of the invention is that the inventive modified shear beam arrangement now serves as a passive force introduction element with a length compensation or balancing function.

Throughout this specification, the term "hydraulic cylinder" refers to a hydraulic piston-cylinder device having any suitable structure.

BRIEF DESCRIPTION OF THE DRAWINGS

In order that the invention may be clearly understood, it will now be described in connection with an example embodiment thereof, with reference to the accompanying drawings, wherein:

FIG. 1 is a schematic front elevation view of a compression and shear testing apparatus according to the invention, for testing a curved aircraft component as a test component;

FIG. 2 is a side sectional view of the inventive apparatus along the section line II—II in FIG. 1;

FIG. 2A is an enlarged detail view of the detail area IIA of FIG. 2;

FIG. 3 is a side sectional view of the inventive apparatus along the section line III—III in FIG. 1; and FIG. 3A is an enlarged detail view of the detail area or portion IIIA in FIG. 3.

DETAILED DESCRIPTION OF A PREFERRED EXAMPLE EMBODIMENT AND OF THE BEST MODE OF THE INVENTION

The inventive testing apparatus for compression and shear testing of a test component such as a curved aircraft component 1 (e.g. an aircraft fuselage shell component), includes an arrangement for applying a vertically directed compression force $F_{DR}$ (see FIG. 1), an arrangement for applying an upwardly directed shear force $F_{SV1}$ to one vertical edge of the component 1 (see FIG. 3), and another arrangement for applying a downwardly directed vertical shear force $F_{SV2}$ to the opposite vertical edge of the component 1 (see FIG. 2). The inventive apparatus shares many features and a basic construction with the conventional apparatus that has been described above in the Background Information section, and modifies and adds certain new inventive features and components relative to the conventional apparatus.

The main compression load $F_{DR}$ is introduced vertically into the test component such as an aircraft component 1 through a force introduction table 2, which is moved by a force-regulated hydraulic cylinder 16, preferably in a vertical direction, toward a pressure plate 3 that acts as a counter-support, with the aircraft component 1 received between the force introduction table 2 and the pressure plate 3. To introduce the compressive force into the aircraft component 1, the component 1 is provided with special rim or edge reinforcements, so that the compressive force between the force introduction table 2 and the pressure plate 3 can be introduced into the body of the component 1 without damaging its upper and lower edges.

The pressure plate 3 is secured, e.g. bolted, to a head frame 15, which may be a stationary component of the machine frame. On the other hand, the hydraulic cylinder 16 is supported on a base that is in turn supported on a transverse girder which is supported from the machine frame by pivotally connected tension rods with integrated tensile force measuring transducers such as load cells (not shown). Additionally, a horizontal shear component can be introduced into the aircraft component 1 by two hydraulic cylinders (not shown) that are pivotally or articulately connected to the force introduction table 2.

Vertical shear forces including an upwardly directed shear component $F_{SV1}$ and a downwardly directed shear component $F_{SV2}$ are introduced into the opposite vertical edges of the aircraft component 1 by two shear beams 5 and 4, respectively (see FIGS. 3 and 2). These shear beams 4 and 5 may include integrated force-regulated multi-chamber hydraulic cylinders 6 and 7 (shown in detail in FIGS. 2A and 3A). In the inventive apparatus, these integrated hydraulic cylinders 6 and 7 are preferably not used actively to generate the shear forces $F_{SV1}$ and $F_{SV2}$ but rather are used passively to transmit the shear forces generated by further cylinders (described in detail below), while compensating any uneven length changes of the two sides of the aircraft component 1 during the compression loading thereof. The hydraulic cylinders 6 and 7 are integrated into the shear beams 4 and 5, and particularly are installed pair-wise at a spacing or raster of e.g. 100 mm in the shear beams 4 and 5 extending along the vertical edges of the aircraft component 1. For introducing the loads from the shear beams 4 and 5 into the aircraft component 1, T-shaped load introduction brackets or fixtures are secured, e.g. screwed or bolted, to the aircraft component 1 along the vertical edge portions or margins thereof, similarly at a spacing or raster of 100 mm.

The inventive apparatus especially includes improvements in the two arrangements for generating and applying the upwardly and downwardly directed shear forces to the aircraft component 1 being tested. More particularly, the upwardly directed vertical shear force $F_{SV1}$ is generated by a first force-regulated hydraulic cylinder 12 arranged above the pressure plate 3. This first hydraulic cylinder 12 is horizontally adjustably supported on the head frame 15 of the apparatus, on which the pressure plate 3 is also secured. The horizontally adjustable support of the first cylinder 12 on the head frame 15 can be achieved in any conventionally known manner, as schematically indicated in FIGS. 1 and 3, for example through mounting on a rail via rollers, or slides, or the like, whereby the precise horizontal position of the first hydraulic cylinder 12 can be adjusted, for example by a threaded spindle or screw adjustment device 17.

The head frame 15 and the hydraulic cylinder 12 are arranged concentrically over the load introduction point of the aircraft component 1 that is to be tested (see e.g. the vertical center planes in FIGS. 1 and 3). The force generated by the first hydraulic cylinder 12 is transmitted to the first shear beam 5 by two laterally arranged tension rod assemblies including tension rods 9 provided with or connected to tensile force measuring transducers or load cells 8 (see FIGS. 1 and 3). The tension rod assemblies extend substantially parallel to one another, at opposite sides (edges) of the pressure plate 3, or with the pressure plate 3 extending transversely therebetween, as shown in FIGS. 1 and 3. Each one of the tension rods 9 is respectively connected through one of the tensile force measuring transducers 8 to the housing or bracket 7A of the shear beam 5 in a rotatable or pivotal manner. The shear beam 5 may include a hydraulic cylinder 7 integrated therein as described above (see FIG. 3A). The housing or bracket 7A may then be a housing or bracket 7A of the integrated hydraulic cylinder 7 of the shear beam 5, such that the cylinder 7 is connected in force-transmitting series between the tension rod assemblies and the component-engaging fixture of the shear beam. Such an integrated hydraulic cylinder 7 is not absolutely necessary in the inventive arrangement including the first hydraulic cylinder 12 for generating the upwardly directed shear force $F_{SV1}$.

As shown in FIGS. 1 and 2, the downwardly directed vertical shear force $F_{SV2}$ is generated by two second force-regulated hydraulic cylinders 13 that are pivotally or articulately connected to the second shear beam 4 on two opposite sides thereof. In this example embodiment, the hydraulic cylinders 13 are respectively directly braced or supported on the pressure plate 3 at the upper ends of the cylinders 13. The two second hydraulic cylinders 13 respectively form a part of two compression strut arrangements 11, wherein the cylinders 13 are respectively further connected through two compression force measuring transducers or load cells 10 in a rotatable or pivotal manner to the two opposite sides of the housing or brackets 6A of the second shear beam 4 (see FIG. 2). The second shear beam 4 may include a hydraulic cylinder 6 integrated therein as described above (see FIG. 2A). In that case, the housing or bearing brackets 6A of the shear beam 4 may be a housing or bearing brackets 6A of the hydraulic cylinder 6, so that the cylinder 6 is connected in force-transmitting series between the compression strut arrangements 11 and the component-engaging fixture of the second shear beam 4.

Thus, the two tension rods 9 and the two tensile force measuring transducers 8 together respectively form two tension rod assemblies that connect the first hydraulic cylinder 12 to the first shear beam 5. Similarly, the two second hydraulic cylinders 13 and the two compressive force measuring transducers 10 together respectively form two compression strut assemblies 11 between the pressure plate 3 and the second shear beam 4. As can be seen by comparing FIGS. 1, 2 and 3, the pressure plate is relatively narrower at a right end portion thereof (FIG. 3) to better accommodate the tension rods 9 extending at opposite sides or edges thereof, and is relatively wider at a left end portion thereof (FIG. 2) to support the second hydraulic cylinders 13 braced or supported thereagainst.

The above described hydraulic cylinders are operated in a 210 bar pressurized hydraulic system. The above described arrangement of the shear force introduction elements makes it possible in an advantageous manner, to carry out the required load introduction process with a high shear load. In other words, the inventive arrangement with the first cylinder 12 and the two second cylinders 13 achieves higher shear loads than the conventionally known apparatus.

As is conventionally known, the various force measuring transducers, e.g. 8 and 10, measure the forces being applied to the test component 1. The behavior of the component 1 under progressively increasing compression load $F_{DR}$ and shear load $F_{SV1}$ and $F_{SV2}$ can be observed and/or tested, for example up to the point of failure of the component 1.

Although the invention has been described with reference to specific example embodiments, it will be appreciated that it is intended to cover all modifications and equivalents within the scope of the appended claims. It should also be understood that the present disclosure includes all possible combinations of any individual features recited in any of the appended claims.

What is claimed is:

1. A testing apparatus for compression and shear testing of a test component that is to be tested, comprising:
   a pressure plate;
   a force introduction table that is movably arranged relative to said pressure plate to allow relative movement thereof in a compression direction, wherein said pressure plate and said force introduction table are adapted to receive the test component therebetween;
   a compression loading hydraulic cylinder that is connected to and acts on at least one of said force introduction table and said pressure plate, and that is adapted to cause the relative movement of said force introduction table relative to said pressure plate in said compression direction so as to apply a compression load to the test component in said compression direction;
   a first securing fixture that is adapted to be secured to the test component;
   a second securing fixture that is adapted to be secured to the test component spaced apart from said first securing fixture;
   a first actively drivable hydraulic cylinder that is supported relative to said pressure plate and that is arranged on a side of said pressure plate opposite said force introduction table;
   two first passive non-driven hydraulic cylinders;
   two tension rod assemblies that are respectively arranged in series with said two first passive non-driven hydraulic cylinders and that extend spaced apart from one another on opposite sides of said pressure plate to connect said first actively drivable hydraulic cylinder to said first securing fixture, wherein said first actively drivable hydraulic cylinder is adapted to generate and apply a first shear force through said tension rod assemblies and said first passive non-driven hydraulic cylinders and said first securing fixture to the test component in a first shear direction; and
   two compression strut arrangements that are supported relative to said pressure plate and are connected respectively to opposite sides of said second securing fixture, wherein said two compression strut arrangements respectively include two second passive non-driven hydraulic cylinders, and two second actively drivable hydraulic cylinders that are adapted to generate and apply a second shear force through said second passive non-driven hydraulic cylinders and said second securing fixture to the test component in a second shear direction opposite said first shear direction.

2. The testing apparatus according to claim 1, wherein said apparatus is arranged so that said compression load in said compression direction, said first shear force in said first shear direction, and said second shear force in said second shear direction all lie parallel to each other in a single common load plane.

3. The testing apparatus according to claim 1, wherein said pressure plate is above said force introduction table, said first actively drivable hydraulic cylinder is above said pressure plate, and said apparatus is arranged so that said compression direction is oriented vertically, said first shear direction is vertically upward, and said second shear direction is vertically downward.

4. The testing apparatus according to claim 1, wherein said first and second securing fixtures extend vertically and parallel to one another, and are adapted to be arranged along and secured to opposite vertical edge portions of the test component.

5. The testing apparatus according to claim 1, wherein said first securing fixture is a component of a first shear beam, said first passive non-driven hydraulic cylinders comprise first integrated hydraulic cylinders that are integrated in said first shear beam and are connected to said first securing fixture, said second securing fixture is a component of a second shear beam, and said second passive non-driven hydraulic cylinders comprise second integrated hydraulic cylinders that are integrated in said second shear beam and are connected to said second securing fixture.

6. The testing apparatus according to claim 5, wherein said first integrated hydraulic cylinders are connected in force-transmitting series between said first securing fixture and said tension rod assemblies, and said second integrated hydraulic cylinders are connected in force-transmitting series between said second securing fixture and said compression strut arrangements.

7. The testing apparatus according to claim 6, wherein said first and second integrated hydraulic cylinders are adapted to passively compensate length changes of the test component between said force introduction table and said pressure plate, said length changes arising due to the compression load applied to the test component.

8. The testing apparatus according to claim 1, further comprising a machine frame including a head frame to which said pressure plate is secured, and wherein said first actively drivable hydraulic cylinder is movably mounted on a side of said head frame opposite said pressure plate such that said first actively drivable hydraulic cylinder is movable and selectively positionable relative to said head frame and relative to said pressure plate in a direction perpendicular to said compression direction.

9. The testing apparatus according to claim 8, wherein said head frame is arranged concentrically above a load introduction center point of said compression load and said first and second shear forces being introduced into the test component.

10. The testing apparatus according to claim 1, wherein said two tension rod assemblies are parallel to one another with said pressure plate extending therebetween.

11. The testing apparatus according to claim 1, wherein each one of said tension rod assemblies respectively comprises a respective tension rod and a respective tensile force measuring transducer connected mechanically in series with one another between said first actively drivable hydraulic cylinder and said first securing fixture.

12. The testing apparatus according to claim 11, wherein each said tension rod is connected to said first actively drivable hydraulic cylinder and each said tensile force measuring transducer is pivotably connected to said first securing fixture.

13. The testing apparatus according to claim 1, wherein said two compression strut arrangements respectively further include two compression force measuring transducers connected mechanically in series respectively with said two second actively drivable hydraulic cylinders between said pressure plate and said second securing fixture.

14. The testing apparatus according to claim 13, wherein said second actively drivable hydraulic cylinders are supported directly against a side of said pressure plate facing toward said force introduction table, and said compression force measuring transducers are pivotably connected to said second securing fixture.

15. The testing apparatus according to claim 1, wherein said pressure plate is relatively narrower at a first end portion thereof to fit between said tension rod assemblies and relatively wider at a second end portion thereof to support said two compression strut arrangements.

16. A shear testing arrangement for shear testing a test component, comprising:
a support structure having opposite first and second sides;
first and second fixtures located at said first side of said support structure and respectively adapted to be fixed to opposite first and second edge portions of the test component;
a first actively drivable hydraulic cylinder arranged on and supported against said second side of said support structure;
two tension rod assemblies that are connected to and extend between said first actively drivable hydraulic cylinder and said first fixture, and that each respectively include a tension rod and at least a first passive non-driven hydraulic cylinder in series with said tension rod; and
two compression strut arrangements that are arranged on and supported against said first side of said support structure, and that extend between said support structure and said second fixture, and that are connected to said second fixture, and that each respectively comprise a respective second actively drivable hydraulic cylinder and at least a second passive non-driven hydraulic cylinder in series with said second actively drivable hydraulic cylinder.

17. The shear testing arrangement according to claim 16, wherein said passive non-driven hydraulic cylinders include plural cylinders arranged in pairs and spaced apart in a direction along the edge portions of the test component, and said fixtures include plural brackets respectively connected to said plural cylinders and adapted to be connected to the edge portions of the test component.

18. The shear testing arrangement according to claim 16, wherein said actively drivable hydraulic cylinders are connected to a force-regulated active hydraulic system, said passive non-driven hydraulic cylinders are connected to a passive hydraulic system, and said passive hydraulic system is pressurized to a higher pressure than said active hydraulic system.

19. A method of compression and shear testing a test component, comprising steps:
a) generating a compression force and applying said compression force to said test component so as to compress said test component with a compression in a compression direction;
b) generating a first shear force with a first actively driven hydraulic cylinder arrangement;
c) transmitting said first shear force through a first passive non-driven hydraulic cylinder arrangement and applying said first shear force to said test component so as to shear load said test component in a first shear direction;
d) generating a second shear force with a second actively driven hydraulic cylinder arrangement; and
e) transmitting said second shear force through a second passive non-driven hydraulic cylinder arrangement and applying said second shear force to said test component so as to shear load said test component in a second shear direction opposite said first shear direction;
wherein said passive non-driven hydraulic cylinder arrangements passively compensate and adapt to a dimensional change of said test component arising due to said compression thereof.

* * * * *